United States Patent [19]
Völkel et al.

[11] Patent Number: 6,057,383
[45] Date of Patent: May 2, 2000

[54] DENTAL MATERIAL BASED ON POLYMERIZABLE WAXES

[75] Inventors: Thomas Völkel, Lindau, Germany; Gerhard Zanghellini, Schaan, Liechtenstein; Karl Fischer, Arbon, Switzerland; Norbert Moszner, Eschen; Volker Rheinberger, Vaduz, both of Liechtenstein

[73] Assignee: Ivoclar AG, Liechtenstein

[21] Appl. No.: 08/878,050

[22] Filed: Jun. 18, 1997

Related U.S. Application Data

[60] Provisional application No. 60/025,542, Sep. 6, 1996.

[30] Foreign Application Priority Data

Jun. 18, 1996 [DE] Germany ............ 196 26 356

[51] Int. Cl.[7] .................. A61K 6/00; C08L 33/06
[52] U.S. Cl. .................. 523/116; 523/109; 523/115; 523/120; 524/560; 524/563; 526/318.3
[58] Field of Search ............... 523/115, 116, 523/109, 120; 524/560, 563; 526/318.3

[56] References Cited

U.S. PATENT DOCUMENTS 4,711,913 12/1987 Tateosian et al. ............ 523/115
5,037,473 8/1991 Antonucci ............ 106/35
5,171,763 12/1992 Ohno et al. ............ 523/116

FOREIGN PATENT DOCUMENTS

| 0 508 095 A2 | 10/1992 | European Pat. Off. . |
| 0 537 774 A1 | 4/1993 | European Pat. Off. . |
| 0 630 640 A1 | 12/1994 | European Pat. Off. . |
| 39 38 359 A1 | 5/1990 | Germany . |
| 50-105751 | 8/1975 | Japan . |
| 57-130907 | 8/1982 | Japan . |
| 64-87608 | 3/1989 | Japan . |

*Primary Examiner*—Andrew E. C. Merriam
*Attorney, Agent, or Firm*—Nixon Peabody LLP

[57] ABSTRACT

The invention relates to dental materials based on wax-like polymerizable substances. The dental materials contain (a) 0 to 70 wt. % of at least one polymerizable monomer and/or oligomer; (b) 0.1 to 5 wt. % of at least one polymerization initiator; (c) 0 to 60 wt. % of one or more fillers, (d) at least 20 wt. % of the wax-like polymerizable substance. They can be kneaded at room temperature and can be modelled in non-polymerized state without additional heating, like conventional waxes. On polymerization, the wax component is covalently incorporated into the polymer. The dental materials are suitable for producing temporary and permanent dental prostheses.

16 Claims, No Drawings

DENTAL MATERIAL BASED ON POLYMERIZABLE WAXES

This application claims the benefit of U.S. Provisional patent application Ser. No. 60/025,542, filed Sep. 6, 1996.

FIELD OF INVENTION

The present invention relates to dental materials based on polymerizable waxes, which are particularly suitable as materials for temporary and permanent dental prostheses, inlays and crowns.

BACKGROUND OF THE INVENTION

The term wax is a collective term for a series of natural and synthetic substances. Generally understood by this term are materials which are already easily plastically mouldable below their melting range or softening range, have a translucent to opaque appearance, melt without decomposition above 40° C. and already produce liquids of relatively low viscosity slightly above the melting point and which possess a greatly temperature-dependent consistency and solubility. Furthermore, waxes can mostly be polished under light pressure (Ullmann's Enzyklopädie der Technischen Chemie, 4th edition, volume 24, Verlag Chemie, Weinheim 1989).

Waxes are used in the dental field as modelling, casting, occlusion or adhesive waxes. Mixtures of natural waxes and synthetic waxes are used almost exclusively, the physical properties of the waxes being geared to the desired use (K. Körber, K. Ludwig, Zahnärztliche Werkstoffe und Technologie, G. Thieme Verlag, Stuttgart, 1982, page 90). For example, a modelling wax suitable for modelling pre-shaped parts should be easy to mould and have as good a dimensional stability as possible at the temperature of the mouth. Mixtures of paraffin wax, stearin wax, Japan wax and beeswax are suitable for this purpose.

Conventional waxes are generally heated for processing. Curing takes place by the wax solidifying on subsequent cooling. In this case, relatively large, uncontrollable volume changes generally occur. Furthermore, conventional waxes have the disadvantage that they easily break when being removed from the model and change their shape under even relatively slight mechanical and above all thermal stress.

In order to avoid these disadvantages, mixtures of natural and partially or wholly synthetic waxes with polymerizable monomers or oligomers such as polyfunctional acrylates and methacrylates have recently been used. These mixtures can be specifically cured after treatment and then have a higher mechanical stability than the pure waxes.

For example, mixtures of polyethylene waxes with styrene or acrylate monomers are disclosed in JP-A-92/4748 (C.A. 120 (1993) 136156) and JP-A-91/330047 (C.A. 119 (1993) 282306). Furthermore, photopolymerizable waxes for the dental field based on mixtures of natural or synthetic waxes with conventional acrylic compounds and photoinitiators are described in JP-A-90/312256 (C.A. 128 (1992) 27523). The disadvantages of these mixtures are that conventional dental waxes and dental crosslinker monomers do not mix well with one another and that above all the wax is not incorporated into the polymer network on polymerization. The result may therefore be the formation of wax domains, i.e. a multiphase system is formed, the mechanical strength of which is accordingly low.

EP-B-0 110 193 discloses wax-free wax substitutes for producing casting models. These compositions are based on mixtures of di- or polyfunctional meth- or acrylic acid esters, a photoinitiator and optionally a photoactivator and organic fillers. On account of the composition of the materials claimed in EP-B-0 110 193, they do not exhibit any wax-like properties, i.e. the materials cannot be modelled like waxes and consequently the dental technician must replace the usual wax technique with a layer technique which involves a lot of work. Changes or adjustments to the model can then no longer be made, since curing takes place by polymerization after application of the respective layer. Furthermore, this process has the disadvantage that thin layers can only be produced using slightly filled or unfilled mixtures of di- or polyfunctional (meth)acrylic acid esters, during the polymerization of which a considerable volume contraction results.

EP-B-0 380 116 discloses mixtures which, in order to influence the expansion behaviour of the moulding compounds, additionally contain an organic compound having a boiling point and/or a sublimation point in the range above 150° C. and which does not react with the organic polymerizable composition. The named compositions are characterized in particular by the fact that they leave no residues upon combustion.

U.S. Pat. No. 5,403,188 discloses thermoplastic moulding compounds which are suitable for the production of dental impressions. The compounds contain a polymeric thermoplastic material, preferably a polycaprolactone, a polymerizable resin, an initiator and optionally a filler. They are solid at 38° C. and practically not mouldable and they are heated for processing. Curing then takes place by cooling. After the impression has been produced, the compounds are additionally cured by a radical polymerization. The materials have the disadvantage that they only melt down to form highly viscous products. Dental shaping is extremely difficult since the materials are not only viscous in the molten state, but also very sticky.

It is the object of the invention to provide wax-like dental materials which do not have the above-named disadvantages and are also suitable in particular for producing temporary and permanent prostheses.

SUMMARY OF THE INVENTION

The object is achieved by dental materials based on polymerizable waxes which contain a) 0 to 70 wt. %, preferably 5 to 70 wt. %, particularly preferably 5 to 60 wt. % and quite particularly preferably 20 to 50 wt. %, of at least one polymerizable monomer and/or oligomer;

b) 0.1 to 5 wt. %, preferably 0.2 to 2.0 wt. %, of at least one polymerization initiator;

c) 0 to 60 wt. %, preferably 0 to 50 wt. % and particularly preferably 0 to 30 wt. %, of fillers; and d) at least 20 wt. %, preferably at least 40 wt. %, of a wax-like polymerizable substance.

DETAILED DESCRIPTION OF THE INVENTION

Suitable polymerizable monomers and oligomers are known for example from DE-C-3 941 629 or DE-A-4 029 230. Compounds which have a crosslinking effect such as di-, tri- or tetraethylene glycol di(meth)acrylate, decanediol di(meth)acrylate, bisphenol-A-di(meth)acrylate, trimethylolpropane tri(meth)acrylate, pentaerythritol tetra(meth)acrylate, 2,2-bis(4-methacryloyloxy-2-hydroxypropoxy)-phenylpropane (bis-GMA) and the reaction product of 1 mol of 2,2,4-trimethylhexamethylene diisocyanate with 2 mol of 2-hydroxyethyl (meth)acrylate and mixtures of these monomers are preferred.

Suitable polymerization initiators are known for example from DE-A-4 029 230. Preferred initiators are camphor quinone, 9,10-phenanthrenequinone or diacetyl. Furthermore, the polymerization initiators can be combined with a suitable reducing agent. Suitable for this purpose are in particular 4-dimethylamino-benzoate, N,N'-(2-cyanoethyl)methylaniline, triethanolamine or 2-(dimethylamino)ethyl methacrylate.

The dental materials according to the invention can contain up to 60 wt. % of fillers, but dental materials containing little or no filler are preferred. The fillers are used to increase mechanical strength, to reduce polymerization shrinkage and to control viscosity. Preferred fillers are known for example from DE-C-3 941 629. Particularly preferred are fillers in the form of amorphous spherical materials based on mixed oxides of $SiO_2$, $ZrO_2$ and/or $TiO_2$, microfine fillers such as pyrogenic silicic acid or precipitated silicic acid, and macro or mini fillers such as quartz powder, glass ceramic powder or glass powder.

Preferred as wax-like polymerizable substances are those compounds which represent a longer-chained carboxylic acid, a carboxylic acid derivative, an OH-functionalized compound and/or a derivative of an OH-functionalized compound and which have one or more polymerizable groups. Preferred carboxylic acid derivatives are the esters with polymerizable alcohols, preferred OH-functionalized compounds are alcohols. Preferred as derivatives of the OH-functionalized compounds are the esters with polymerizable carboxylic acid derivatives. The wax-like polymerizable substances are preferably used in monomeric form. Suitable wax-like polymerizable substances are in some cases commercially available, such as for example stearyl acrylate (melting point 23° C., Christ Chem.), PEG-1000-dimethacrylate (melting point 20° C.) and PEG-4000-diacrylate (melting point 52° C., both from Polysciences, Inc.), or can be produced by chemical modification of suitable carboxylic acids and alcohols.

Preferred for this purpose are carboxylic acids with a melting point of above 60° C., in particular those with a chain length of 16 to 32 carbon atoms. Palmitic acid (melting point: 64° C.), stearic acid (melting point: 69° C.), eicosanoic acid ($C_{20}H_{40}O_2$; melting point: 74–76° C.), docosanoic acid ($C_{22}H_{44}O_2$; melting point: 80–82° C.), tricosanoic acid ($C_{23}H_{46}O_2$; melting point: 75–83° C.), hexacosanoic acid ($C_{26}H_{52}O_2$; melting point: 87–89° C.), heptacosanoic acid ($C_{27}H_{54}O_2$; melting point: 88–89° C.) or octacosanoic acid ($C_{28}H_{56}O_2$; melting point: 61–63° C.) are quite particularly preferred. Mixtures of these carboxylic acids are also suitable. Mixtures of palmitic or stearic acid with hexacosanoic or heptacosanoic acid are preferred. A particularly suitable starting material for producing the wax-like polymerizable substances according to the invention is Hoechst-Wachs S (Hoechst, melting point 80° C.) which is a mixture of longer-chained aliphatic carboxylic acids ($C_{16}$ to $C_{36}$).

Longer-chained alcohols with a melting point of above 55° C. as starting materials for producing the polymerizable wax-like substances are preferred as alcohols, in particular those with a chain length of 18 to 32 carbon atoms. Quite particularly preferred are 1,2-octadecanediol ($C_{18}H_{38}O_2$; melting point: 74–76 ° C.), 1-eicosanol (($C_{20}H_{41}OH$; melting point: 64–66° C.), 1-docosanol ($C_{22}H_{45}OH$; melting point 65–72° C.) or 1-hexacosanol ($C_{26}H_{53}OH$; melting point: 79–81° C.), and Hoechst-Wachs KST (Hoechst, melting point 57–59° C.; based on OH-terminated polyethylene oxide).

Starting from the above wax-like carboxylic acids, the introduction of polymerizable groups preferably takes place by reaction with suitable unsaturated compounds, in particular vinyl, (meth)acrylic or allyl compounds, according to known methods of organic chemistry. Polymerizable methacrylate groups can be introduced for example after activation of the COOH groups e.g. with chloroformate according to the method of the mixed anhydrides in a single-pot reaction by reaction with 2-hydroxyethyl methacrylate (HEMA), hydroxypropyl methacrylate or glycerol dimethacrylate (GDMA). Furthermore, introduction of methacrylic groups can also take place by directly reacting the wax-like carboxylic acids with methacrylic acid-2,3-epoxypropyl ester (GMA).

Starting from the above wax-like OH-functionalized compounds, the introduction of polymerizable groups such as e.g. methacrylic groups is possible for example simply by their azeotropic esterification with methacrylic acid or by acylation with methacrylic acid chloride or methacrylic acid anhydride. Furthermore, the reaction of the OH-functionalized compounds with 2-isocyanatoethyl methacrylate (IEMA) is particularly suitable.

Analogously thereto, the COOH- or OH-functionalized wax-like starting compounds can also be reacted with other suitable unsaturated compounds, so that other polymerizable groups such as acrylic, allyl, vinyl, vinyl ether or styryl groups are introduced in place of methacrylic radicals. Suitable reagents are e.g. 2-hydroxyethyl acrylate, acrylic acid, acrylic acid chloride, allyl alcohol, 3-buten-1-ol, 2-hydroxyethyl vinyl ether, 4-hydroxymethyl styrene or 4-vinyl benzoic acid. Methacrylate, acrylate and styryl groups are preferred as polymerizable groups.

In order to produce the dental materials according to the invention, the starting materials are mixed in the stated quantities. The dental materials can contain other materials in addition to the named components, such as for example pigments or dyes. Furthermore, mixtures of different wax-like polymerizable substances can be used.

The dental materials according to the invention have a wax-like consistency, i.e. they are kneadable to ductile-hard at room or body temperature and can be modelled, plastically moulded or otherwise worked decomposition-free in non-polymerized state without additional heating, like conventional waxes. They exhibit an opaque to partially translucent appearance and can be polished under light pressure. Above ca 40° C. they yield slightly viscous, liquid melts which are not prone to cobwebbing.

After modelling, the materials can be cured by polymerization. The curing preferably takes place by photopolymerization. The wavelength of the light which is necessary to trigger the photopolymerization depends on the photoinitator used, photoinitiators with an excitation wavelength in the wavelength range from 390 to 500 nm being preferred. The photopolymerization can take place in stages at increasing temperatures, i.e. the dental material is initially cured at room temperature by irradiation and then post-polymerized in the temperature range from ca 40 to 80° C., whereby the strength of the materials increases further.

A particular advantage of the wax-like polymerizable substances according to the invention is that they are characterized by a low polymerization shrinkage, which is very advantageous for the dimensional stability of the total material. The pure polymerizable waxes preferably have a polymerization shrinkage of at most 2.2 vol. %, whereas e.g. methyl methacrylate, which is the monomer component of most prosthesis materials, has a volume shrinkage of 20.7 vol. %.

The wax component is covalently incorporated into the formed polymer during polymerization so that a monophase system forms. The cured dental materials therefore have a much greater strength after polymerization than known wax-containing materials. By combining the wax-like polymerizable substances according to the invention with other monomers preferably having a crosslinking effect, dental materials can be produced which after polymerization approach the E modulus of conventional polymethyl methacrylate (PMMA) materials. Thus a preferred dental material consisting of 66.3 wt. % wax monomer, 32.9 wt. % pentaerythritol tetraacetate and 0.8 wt. % of a photoinitiator combination has an E modulus of ca 1.9 GPa after polymerization.

The dental materials according to the invention exhibit a much higher stability in the mouth than conventional materials and are therefore also suitable, unlike known materials, for producing temporary and permanent prostheses.

The dental materials according to the invention allow a perceptible simplification of the production process e.g. of whole prostheses. It has been customary up to now in the production of whole prostheses initially to produce a wax prosthesis which is adapted to the patient in the mouth. As soon as the result is satisfactory, the wax prosthesis is converted by the "lost wax technique" into a permanent PMMA prosthesis. This additional process step can be avoided using the dental materials according to the invention since the prosthesis can be polymerized and elaborated directly after the adaptation. This means a considerable reduction in labour expenditure and therefore in the costs arising in the production of prostheses.

A further area of application of the dental materials according to the invention is in the production of temporary crowns, bridges and inlays. On account of their good mouldability in the patient's mouth, the dental materials according to the invention can be adapted to the tooth stump treated, whereby the material can be shaped by simple scraping and then cured by polymerization. Reinforcements can be inserted into the material prior to polymerization to strengthen bridges in particular.

EXAMPLES

Example 1
Synthesis of Polymerizable Waxes by Esterification of Hoechst-Wachs S with HEMA A mixture of 70 g of Hoechst-Wachs S (186.7 mmol), 22.6 g of collidine (186.7 mmol), 20.3 g of chloroformic acid ethyl ester (186.7 mmol) and 1000 ml of toluene is stirred for 72 hrs at 60° C. with exclusion of moisture. 24.4 g of HEMA (186.7 mmol) and some p-toluenesulphonic acid are added as catalyst and the whole is then stirred for 3 days at 60 ° C. The reaction preparation is then filtered at 60° C. and the filtrate is left to stand in a refrigerator for 12 hrs at 4° C., whereby a white voluminous precipitate is formed which is dried over anhydrous $CaCl_2$ in a desiccator after separation and washing with some acidified water and with ethanol. Ca 60 g (yield 70%) of a wax-like solid are obtained (melting range: 47–61° C., determined by differential scanning calorimetry (DSC)).

The viscosity of the wax is ca 0.5 Pa·s above the melting range (measured at 85° C.; the viscosity no longer decreases significantly with the temperature from ca 61° C.).

Evaluation of the $^1$H-NMR spectrum shows that 48% of the COOH groups are esterified with HEMA.

$^1$H-NMR (CDCl$_3$): δ=5.6 and 6.2 (2s, =CH$_2$), 4.3 (t, CH$_2$O), 2.2 (t, CH$_2$COO), 1.9 (s, CH$_3$) and 1.2 to 1.4 ppm (broad, CH$_2$).

Example 2
Synthesis of a Polymerizable Wax by Esterification of Hoechst-Wachs S with GDMA Analogously to Example 1, a mixture of 140 g of Hoechst-Wachs S (373.4 mmol), 45.2 g of collidine (373.4 mmol), 40.5 g of chloroformic acid ethyl ester (373.4 mmol) and 1000 ml of toluene is reacted with 85.2 g (373.4 mmol) of GDMA. After the treatment, 80 g (yield 50%) of a wax-like solid were obtained (melting point 55–70° C.).

$^1$H-NMR (CDCl$_3$): δ=5.6 and 6.2 (2s, =CH$_2$), 4.0 to 4.5 (m, CH$_2$O and CHO), 2.2 (t, CH$_2$COO), 1.9 (s, CH$_3$) and 1.2 to 1.6 ppm (broad, CH$_2$). IR (Film): 3450 (O—H), 2918 (C—H), 1737 (C=O), 1638 (C=C) and 1171 cm$^{-1}$ (C—O).

Example 3
Synthesis of a Polymerizable Wax By Reaction of Hoechst-Wachs S with GMA A mixture of 40 g (0.11 mol) of Hoechst-Wachs S, 44.6 g (0.31 mol) of GMA, 0.7 g of 1,4-diazabicyclo[2.2.2]octane and 600 ml of toluene is stirred for 5 days at 65° C. After the preparation has been concentrated to ca 200 ml, the mixture is left to stand overnight in a refrigerator. The formed precipitate is filtered off, washed with some acidified water and with ethanol and then dried over anhydrous $CaCl_2$ in a desiccator. Ca 51 g (yield: almost 100%) of a wax-like solid are obtained (melting point: 40–67° C., by DSC). Evaluation of the $^1$H-NMR spectrum shows that 90% of the COOH groups have reacted with GMA.

$^1$H-NMR (CDCl$_3$): δ=5.8 and 6.3 (2s, =CH$_2$), 4.3 to 4.7 (m, HOCH-CH$_2$), 2.4 to 2.6 (m, CH$_2$-C=O), 2.2 (s, CH$_3$) and 1.9 to 2.1 ppm (broad, CH$_3$). IR (Film): 3368 (O—H), 2927 (C—H), 1719 (C=O) and 1638 cm$^{-1}$ (C=C).

Example 4
Synthesis of a Polymerizable Wax by Reaction of Octadecanediol-1,2 with IEMA 7.8 g (50.3 mmol) of IEMA are added dropwise to a solution of 7.4 g (25.6 mmol) of octadecanediol-1,2 and 20 mg of Metatin 812 in 80 ml of THF in such a way that the temperature does not exceed 26° C. After stirring for five days, the solvent is distilled off in vacuo, 14.6 g (yield: 97%) of a wax-like solid being obtained (melting point: 42° C.).

$C_{32}H_{56}N_2O_8$ (596.8) Calc.: C, 64.42 H, 9.53; N, 4.65; Found: C, 64.38; H, 9.41; N, 4.61; $^1$H-NMR (CDCl$_3$): δ=5.6 and 6.1 (2s, =CH$_2$), 5.0 (m, >CHO), 4.2 (t, CH$_2$O), 3.5 (t, CH$_2$N), 1.9 (s, CH$_3$) and 1.1 to 1.3 ppm (broad, CH$_2$). IR (Film): 3365 (N—H), 2835 (C—H), 1720 (C=O) and 1637 cm$^{-1}$ (C=C).

Example 5
Synthesis of a Polymerizable Wax by Reaction of Hoechst-Wachs KST with IEMA A solution of 15 g (10 mmol) of Hoechst-Wachs KST, 2.1 g (20 mmol) of IEMA and 2 drops of di-n-octyl tin dilaurate as catalyst (Metatin 812, Acima AG) in 225 ml of toluene is stirred for 3 days at 60° C. After the solution has been concentrated to 80 ml in vacuo, the mixture is left to stand overnight in a refrigerator. The formed precipitate is filtered off, washed with some acidified water and with ethanol and then dried in a desiccator over anhydrous $CaCl_2$. 6.7 g (yield: 45%) of a wax-like solid are obtained (melting point: 45 ° C.). Evaluation of the $^1$H-NMR spectrum shows that the OH-groups have been practically quantitatively reacted with IEMA.

$^1$H-NMR (CDCl$_3$): δ=5.7 and 5.0 (2s, =CH$_2$), 5.0 (broad, NH), 4.3 (t, CH$_2$O), 3.6 (broad, CH$_2$), 3.5 (m, CH$_2$N), 2.0 ppm (s, CH$_3$). IR (KBr): 2918, 2849 (C—H), 1737 (C=O) and 1637 cm$^{-1}$ (C=C).

Example 6
Substance Polymerization of the Wax-like Monomers 2 g each of wax-like monomer from the above examples are reacted with in each case 10 mg of dibenzoyl peroxide. The polymerization enthalpy resulting on heating from room temperature to 200° C. (10° C./min) is then determined by DSC. On the basis of the polymerization enthalpy of lauryl methacrylate as standard, a complete C=C conversion results for the waxes of Examples 1 and 4, whereas a C=C conversion of 78, 69 and 42 mol. % respectively results for the waxes of Examples 2, 3 and 5. The C=C conversions show that the methacrylate groups of the wax-like monomers can be radically polymerized. Moreover, the volume shrinkage (Δ-V) occurring during polymerization was determined from the difference between the pycnometrically determined densities of wax monomer and polymer. The Δ-V values lie in the range from a minimum of −0.7 vol. % (monomer of Example 2) and a maximum of −2.2 vol. % (monomer of Example 4).

Example 7
Formulations and Properties of Wax-like Dental Materials Based on Wax-like Monomers The dental materials listed in Table 1 are produced by means of a 3-roller mill (all quantities are in wt. %).

Testpieces are then moulded from the dental materials and cured by irradiation in a Spectramat (Vivadent, 10 min). The property values obtained using the bending test according to DIN 53452 and 53457 are given in Table 2.

TABLE 1

Composition of dental materials

| Component | Example 7a | Example 7b | Example 7c |
|---|---|---|---|
| Wax monomer | Example 1: 72.5% | Example 3: 72.0% | Example 2: 66.3% |
| SR-295[a] | 26.7% | 27.2% | 32.9% |
| Camphor quinone | 0.3% | 0.3% | 0.3% |
| CEMA[b] | 0.5% | 0.5% | 0.5% |

[a]Pentaerythritol tetraacrylate
[b]2-cyanoethylmethylaniline

TABLE 2

Properties of dental materials

| | Example 7a | Example 7b | Example 7c |
|---|---|---|---|
| Bending strength (MPa) | 5 | 20 | 12 |
| Flexural E-modulus (MPa) | 1010 | 1320 | 1940 |

Crowns and inlays were modelled using the material according to Example 7c based on the usual wax method and were then cured in a Spectramat. Solid models were obtained with a very good dimensional stability and a thermal dimensional stability that was excellent compared with conventional wax models.

Example 8
Comparative Example

Analogously to Example 7, dental materials were produced using conventional, non-polymerizable waxes (Table 3, all quantities in wt. %).

The production of testpieces was not possible owing to the low strength of the materials; the materials were seriously cracked after irradiation. Mechanical studies could therefore not be carried out.

TABLE 3

Composition of comparison materials with non-polymerizable waxes

| Component | Example 8a | Example 8b |
|---|---|---|
| Wax monomer | Hoechst-Wachs S 66.1% | S-U-Ästhetikwachs-O[c] 66.1% |
| SR-295[a] | 33.1% | 33.1% |
| Camphor quinone | 0.3% | 0.3% |
| CEMA[b] | 0.5% | 0.5% |

[a]Pentaerythritol tetraacrylate
[b]2-cyanoethylmethylaniline
[c]Schuler-Dental

Example 9
Comparative Example

Dental materials with the compositions shown in Table 4 were produced in accordance with U.S. Pat. No. 5,403,188 (Example 1, run nos 1, 12, 13, 16 and 17). No wax-like materials were obtained in this case, but thermoplastic materials which display rubber-like viscosity on melting. Furthermore, the melts are highly viscous (polycaprolactone TONE 767: ca 8500 Pa·s above the melting point (65° C.)) and non-dripping, whereas the wax melts according to the invention exhibit a low viscosity (Example 1: ca 0.5 Pa·s above the melting range) and are liquid.

TABLE 4

Thermoplastic dental materials

| TONE P-767[a] wt. % | Acrylate wt. % | Viscosity at 65° C. (Pa · s) |
|---|---|---|
| 100 | 0 | 8500 |
| 70 | 30[b] | 1140 |
| 55 | 45[b] | 1540 |
| 70 | 30[c] | 100 |
| 55 | 45[c] | 30 |

[a]Polycaprolactone; molecular mass: 40 000 g/mol (Union Carbide)
[b]Ebercryl 230, aliphatic urethane diacrylate resin (UCB Chemicals)
[c]Ebercryl 830, hexafunctional polyester acrylate oligomer (UCB Chemicals)

We claim:

1. A polymerizable wax-like dental material comprising
   (a) 0 to 70 wt. % of at least one polymerizable monomer and/or oligomer;
   (b) 0.1 to 5 wt. % of at least one polymerization initiator;
   (c) 0 to 60 wt. % of one or more fillers,
   (d) at least 20 wt. % of a wax-like polymerizable substance.
2. Dental material according to claim 1, wherein the proportion of component (a) is 5 to 70 wt. %.
3. Dental material according to claim 1, wherein the proportion of component (b) is 0.2 to 2.0 wt. %.
4. Dental material according to claim 1, wherein the proportion of component (c) is 0 to 50 wt. %.
5. Dental material according to claim 1, wherein the dental material comprises at least 40 wt. % of the wax-like polymerizable substance.

6. Dental material according to claim 1, wherein the wax-like polymerizable substance is a long-chained carboxylic acid, a derivative of such a carboxylic acid, a hydroxyl-containing compound and/or a derivative of a hydroxyl-containing compound and has one or more polymerizable groups.

7. Dental material according to claim 6, wherein the wax-like polymerizable substance is the ester of a carboxylic acid with a polymerizable alcohol.

8. Dental material according to claim 7, wherein the carboxylic acid has a melting point of above 60° C.

9. Dental material according to claim 8, wherein the carboxylic acid has a chain length of 16 to 32 carbon atoms.

10. Dental material according to claim 6, wherein the wax-like polymerizable substance is the ester of an alcohol with a polymerizable carboxylic acid derivative.

11. Dental material according to claim 10, wherein the alcohol has a melting point of above 55° C.

12. Dental material according to claim 11, wherein the alcohol has a chain length of 18 to 32 carbon atoms.

13. Dental material according to claim 6, wherein the polymerizable groups are methacrylic, acrylic, allyl, vinyl, vinyl ether and/or styryl groups.

14. A method of producing a dental material comprising:
(a) combining
  (i) 0 to 70 wt. % of at least one polymerizable monomer and/or oligomer;
  (ii) 0.1 to 5 wt. % of at least one polymerization initiator;
  (iii) 0 to 60 wt. % of one or more fillers; and
  (iv) at least 20 wt. % of a wax-like polymerizable substance
  to produce a dental material.

15. The method of claim 14, wherein the wax-like polymerizable substance is a long-chained carboxylic acid, a derivative of such a carboxylic acid, a hydroxyl-containing compound and/or a derivative of a hydroxl-containing compound and has one or more polymerizable groups.

16. The method of claim 14 further comprising:
(b) modelling said dental material; and
(c) curing said dental material by polymerization to produce temporary or permanent dental prostheses, inlays or crowns.

* * * * *